(12) United States Patent
Matta et al.

(10) Patent No.: US 9,833,536 B1
(45) Date of Patent: Dec. 5, 2017

(54) CONTACT LENS DISINFECTING SYSTEM

(71) Applicant: Medivators Inc., Minneapolis, MN (US)

(72) Inventors: John J. Matta, Shoreview, MN (US); Jon Olson, Delano, MN (US); Matt Conlon, Caldwell, NJ (US)

(73) Assignee: Medivators Inc., Minneapolis, MN (US)

( * ) Notice: Subject to any disclaimer, the term of this patent is extended or adjusted under 35 U.S.C. 154(b) by 0 days.

(21) Appl. No.: 15/014,628

(22) Filed: Feb. 3, 2016

Related U.S. Application Data

(60) Provisional application No. 62/111,868, filed on Feb. 4, 2015.

(51) Int. Cl.
*A61L 12/08* (2006.01)
*A61L 12/12* (2006.01)
*B65D 25/08* (2006.01)

(52) U.S. Cl.
CPC ........... *A61L 12/086* (2013.01); *A61L 12/124* (2013.01); *B65D 25/08* (2013.01)

(58) Field of Classification Search
CPC ....... A61L 12/086; A61L 12/124; A61L 25/08
See application file for complete search history.

(56) References Cited

U.S. PATENT DOCUMENTS 4,521,375 A * 6/1985 Houlsby ................ A01N 59/00 134/27
5,919,698 A * 7/1999 Sorensen ............. A61L 12/082 134/901
5,928,606 A * 7/1999 Sugiura ................. A61L 12/086 206/205

FOREIGN PATENT DOCUMENTS

EP 1252819 A1 * 10/2002

* cited by examiner

*Primary Examiner* — Ali Soroush
(74) *Attorney, Agent, or Firm* — Schwegman Lundberg & Woessner, P.A.

(57) ABSTRACT

A contact lens storage system that includes sterilized solution, at least one contract lens, a buffering agent, and a container. The sterilized solution and contact lens are physically separated from the buffering agent. Also described herein are related methods for neutralizing a sterilized contact lens solution, methods of inserting a contact lens onto an eye, and methods of disinfecting and neutralizing a contact lens.

22 Claims, No Drawings

US 9,833,536 B1

CONTACT LENS DISINFECTING SYSTEM

CLAIM OF PRIORITY

This patent application claims the benefit of priority of Matta, et al.'s U.S. Provisional Patent Application Ser. No. 62/111,868, entitled "Contact Lens Disinfecting System." filed on 4 Feb. 2015, which is hereby incorporated by reference herein in its entirety.

BACKGROUND

Disinfecting solutions for the care of contact lenses are well known in the art. Presently marketed peroxide disinfection systems have been around for over twenty-five years with little or no improvement in disinfection profile. Surfactants have been added to assist in protein and lipid cleaning, but little, if any, progress has been made to improve upon the biocidal effectiveness of lens care peroxide systems. Neither have there been any advances in a peroxide disinfectant system. There is a need therefore to improve upon the peroxide systems used in the disinfection and storage of the lenses.

OVERVIEW

The present invention provides for a system that includes: (a) sterilized solution; (b) at least one contact lens located substantially in the sterilized solution; (c) buffering agent: and (d) container that contains the sterilized solution, contact lens, and buffering agent; wherein the sterilized solution and contact lens are physically separated from the buffering agent. In specific embodiments, the system is sterilized and neutralized, effective to store contact lenses.

The present invention also provides for a method for neutralizing a sterilized contact lens solution. The method includes: (i) providing or forming a system including: (a) sterilized solution; (b) at least one contact lens located substantially in the sterilized solution: (c) buffering agent; and (d) container that contains the sterilized solution, contact lens, and buffering agent; to obtain a sterilized contact lens solution, wherein the sterilized solution and contact lens are physically separated from the buffering agent; and (ii) facilitating physical contact between the (1) sterilized solution and contact lens and (2) buffering agent, wherein the contact is effective to neutralize the sterilized contact lens solution.

The present invention also provides for a method of inserting a contact lens onto the outer surface of an eye, the method including: (i) providing or forming a system that includes: (a) sterilized solution; (b) at least one contact lens located substantially in the sterilized solution; (c) buffering agent; and (d) container that contains the sterilized solution, contact lens, and buffering agent; to obtain a sterilized contact lens solution, wherein the sterilized solution and contact lens are physically separated from the buffering agent; (ii) facilitating physical contact between the (1) sterilized solution and contact lens and (2) buffering agent, effective to neutralize the sterilized contact lens solution; (iii) optionally rinsing the contact lens; and (iv) inserting the contact lens onto the outer surface of an eye.

The present invention also provides for a method of disinfecting and neutralizing a contact lens, the method including: (i) providing or forming a system including: (a) sterilized solution; (b) at least one contact lens located substantially in the sterilized solution: (c) buffering agent; and (d) container that contains the sterilized solution, contact lens, and buffering agent; to obtain a sterilized contact lens solution, wherein the sterilized solution and contact lens are physically separated from the buffering agent; and (ii) facilitating physical contact between the (1) sterilized solution and contact lens and (2) buffering agent, effective to neutralize the sterilized contact lens solution. This overview is intended to provide an overview of subject matter of the present patent application. It is not intended to provide an exclusive or exhaustive explanation of the invention. The detailed description is included to provide further information about the present patent application.

DETAILED DESCRIPTION

Reference will now be made in detail to certain claims of the disclosed subject matter, examples of which are illustrated in the accompanying structures and formulas. While the disclosed subject matter will be described in conjunction with the enumerated claims, it will be understood that they are not intended to limit the disclosed subject matter to those claims. On the contrary, the disclosed subject matter is intended to cover all alternatives, modifications, and equivalents, which may be included within the scope of the presently disclosed subject matter as defined by the claims.

References in the specification to "one embodiment." "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The presently disclosed subject matter relates to disinfecting systems for contacts lens. When describing the disinfecting systems for contacts lens, the following terms have the following meanings, unless otherwise indicated.
Definitions Unless stated otherwise, the following terms and phrases as used herein are intended to have the following meanings:

The term "sterile" or "sterilized" refers to state of being free (or essentially free) from disease-causing contaminants (such as bacteria, viruses, fungi, and parasites) or, preventing contact with microorganisms. Sterilization refers to any process that eliminates (removes) or kills all forms of life, including transmissible agents (such as fungi, bacteria, viruses, spore forms, etc.) present on a surface or contained in a fluid. Sterilization can be achieved by applying heat, chemicals, irradiation, high pressure, and filtration or combinations thereof.

The term "contact lens" refers to a thin lens placed directly on the surface of the eye. Contact lenses are considered medical devices and can be worn to correct vision, or for cosmetic or therapeutic reasons.

The term "buffering agent" refers to a weak acid or base used to maintain the acidity (pH) of a solution near a chosen value after the addition of another acid or base. That is, the function of a buffering agent is to prevent a rapid change in pH when acids or bases are added to the solution. Buffering agents are usually added to water to form a buffer solution, which only slightly changes its pH in response to other acids and bases being combined with it, particularly a strong acid or a strong base.

The term "peracetic acid" or "PAA" refers to an organic compound with the formula $CH_3CO_3H$. This organic peroxide is a colorless liquid with a characteristic acrid odor reminiscent of acetic acid. It can be highly corrosive. Peracetic acid is a weaker acid than the parent acetic acid, with a pKa of 8.2.

The term "acetic acid" refers to an organic compound with the chemical formula $CH_3COOH$ (also written as $CH_3CO_2H$ or $C_2H_4O_2$). It is a colorless liquid that when undiluted is also called glacial acetic acid.

The term "1-hydroxyethylidene-1,1-diphosphonic acid" refers to the compound having the molecular formula $C_2H_8O_7P_2$, molecular weight of 206.02, and CAS. Reg. No. 2809-21-4.

The term "pH" refers to a measure of the acidity or basicity of an aqueous solution. Solutions with a pH less than 7 are said to be acidic and solutions with a pH greater than 7 are basic or alkaline. Pure water has a pH very close to 7. Mathematically, pH is the negative logarithm of the activity of the (solvated) hydronium ion, more often expressed as the measure of the hydronium ion concentration.

The term "bicarbonate" refers to an intermediate form in the deprotonation of carbonic acid. It is a polyatomic anion with the chemical formula $HCO_3-$. Bicarbonate serves a crucial biochemical role in the physiological pH buffering system. The prefix "bi" in "bicarbonate" comes from an outdated naming system and is based on the observation that there is two times as much carbonate ($CO_3$) per sodium ion in sodium bicarbonate ($NaHCO_3$) and other bicarbonates as in sodium carbonate ($Na_2CO_3$) and other carbonates.

The term "bisulfate" or "hydrogen sulfate" refers to the ion $HSO_4^-$. An example of a salt containing the $HSO_4^-$ group is sodium bisulfate. $NaHSO_4$. In dilute solutions the hydrogen sulfate ions also dissociate, forming more hydronium ions and sulfate ions ($SO_4^{2-}$).

The term "phosphate" refers to the ion $PO_4^{3-}$, which is as an inorganic chemical is a salt of phosphoric acid. In organic chemistry, a phosphate, or organophosphate, is an ester of phosphoric acid.

The term "thiosulfate" refers to the ion $S_2O_3^{2-}$. The prefix thio-indicates that thiosulfate ion is a sulfate ion with one oxygen replaced by a sulfur.

The term "alkali hydroxide" refers to a class of chemical compounds which are composed of an alkali metal cation and the hydroxide anion ($HO^-$). The alkali hydroxides are: lithium hydroxide (LiOH), sodium hydroxide (NaOH), potassium hydroxide (KOH), rubidium hydroxide (RbOH), and caesium hydroxide (CsOH).

The term "dextrose" refers to a simple aldosic monosaccharide found in plants, having the systematic name (2R, 3S,4R,5R)-2,3,4,5,6-pentahydroxyhexanal.

The term "lecithin" refers to a generic term to designate any group of yellow-brownish fatty substances occurring in animal and plant tissues composed of phosphoric acid, choline, fatty acids, glycerol, glycolipids, triglycerides, and phospholipids (e.g., phosphatidylcholine, phosphatidylethanolamine, and phosphatidylinositol).

The term "polyoxyethylene (20) sorbitan monooleate (Tween 80)" or "polysorbate 80" refers to a nonionic surfactant and emulsifier often used in foods and cosmetics. This synthetic compound (CAS Reg. No. 9005-65-6) is a viscous, water-soluble yellow liquid.

The term "sodium bisulfate" or "sodium hydrogen sulfate" refers to the sodium salt of the bisulfate anion, with the molecular formula $NaHSO_4$. Sodium bisulfate is an acid salt formed by partial neutralization of sulfuric acid by an equivalent of sodium, typically either in the form of sodium hydroxide or sodium chloride. It is a dry granular product that can be safely shipped and stored. The anhydrous form is hygroscopic. Solutions of sodium bisulfate are acidic, with a 1M solution having a pH of <1.

The term "sodium thioglycolate" refers to the sodium salt of thioglycolic acid (TGA), which is the organic compound $HSCH_2CO_2H$.

The term "sodium thiosulfate" refers to the compound $Na_2S_2O_3$.

The term "tryptone" refers to the assortment of peptides formed by the digestion of casein by the protease trypsin.

The term "yeast extract" refers to the common name for various forms of processed yeast products made by extracting the cell contents (removing the cell walls). Yeast extracts in liquid form can be dried to a light paste or a dry powder.

The term "deionized (DI) water" or "demineralized water" refers to water that has had almost all of its mineral ions removed, such as cations like sodium, calcium iron, and copper, and anions such as chloride and sulfate. Deionization is a chemical process that uses specially manufactured ion-exchange resins which exchange hydrogen ion and hydroxide ion for dissolved minerals, which then recombine to form water. Because most non-particulate water impurities are dissolved salts, deionization produces a high purity water that is generally similar to distilled water, and this process is quick and without scale buildup. However, deionization does not significantly remove uncharged organic molecules, viruses or bacteria, except by incidental trapping in the resin. Specially made strong base anion resins can remove Gram-negative bacteria. Deionization can be done continuously and inexpensively using electrodeionization. Three types of deionization currently exist: co-current, counter-current, and mixed bed.

The term "columbia broth" refers to a composition that includes the following ingredients:

| Name | CAS Reg. No. |
| --- | --- |
| Pancreatic digest of casein | 9000-71-9 |
| Peptic digest of animal tissue | 73049-73-7 |
| Yeast enriched peptone | None |
| Sodium chloride | 7647-14-5 |
| Dextrose | 50-99-7 |
| L-Cysteine-HCl | 30925-07-6 |
| Magnesium sulfate | 7487-88-9 |
| Ferrous sulfate | 7782-63-0 |
| Tris-base | 77-86-1 |
| Tris-HCl | 1185-53-1 |
| Sodium carbonate | 6132-02-1 |

The term "potassium dihydrogen phosphate" refers to the compound $KH_2PO_4$.

The term "sodium hydroxide" refers to the compound NaOH.

The term "L-cystine" refers to the (L) form of the amino acid formed by the oxidation of two cysteine molecules that covalently link via a disulfide bond. This organosulfur compound has the formula $(SCH_2CH(NH_2)CO_2H)_2$. It is a white solid that is slightly soluble in water.

The term "tryptone" refers to the assortment of peptides formed by the digestion of casein by the protease trypsin.

The term "sodium chloride" refers to the compound NaCl.

The term "letheen broth" refers to a composition that includes the following substances in the approximate relative amounts: beef extract (5.0 g), proteose peptone No. 3 (10.0 g), polysorbate 80 (5.0 g), lecithin (0.7 g), and sodium chloride (5.0 g).

The term "catalase" refers to a common enzyme found in nearly all living organisms exposed to oxygen (such as vegetables, fruit or animals). It catalyzes the decomposition of hydrogen peroxide to water and oxygen. It is a very important enzyme in protecting the cell from oxidative damage by reactive oxygen species (ROS). Likewise, catalase has one of the highest turnover numbers of all enzymes; one catalase molecule can convert approximately 5 million molecules of hydrogen peroxide to water and oxygen each second. Catalase is a tetramer of four polypeptide chains, each over 500 amino acids long. It contains four porphyrin heme (iron) groups that allow the enzyme to react with the hydrogen peroxide. The optimum pH for human catalase is approximately 7, and has a fairly broad maximum (the rate of reaction does not change appreciably at pHs between 6.8 and 7.5). The pH optimum for other catalases varies between 4 and 11 depending on the species. The optimum temperature also varies by species.

The term "silver nitrate" refers to the compound $AgNO_3$.

The term "solid" refers to one of the four fundamental states of matter (the others being liquid, gas, and plasma). It is characterized by structural rigidity and resistance to changes of shape or volume. Unlike a liquid, a solid object does not flow to take on the shape of its container, nor does it expand to fill the entire volume available to it like a gas does. The atoms in a solid are tightly bound to each other, either in a regular geometric lattice (crystalline solids, which include metals and ordinary ice) or irregularly (an amorphous solid such as common window glass). Reference to a substance being a solid is under ambient conditions (e.g., STP).

The term "pellet" refers to a solid, small, compressed, hard chunk of matter that will dissolve or disintegrate in aqueous fluid within an extended period of time.

The term "pill" refers to a solid, small, cylindrical, piece of matter that will dissolve or disintegrate in aqueous fluid within an extended period of time.

The term "capsule" refers to a solid, small container, containing one or more substances that will dissolve or disintegrate in aqueous fluid within an extended period of time.

The term "tablet" refers to a solid piece of matter that will dissolve or disintegrate in aqueous fluid within an extended period of time, wherein the solid piece of matter is formed by compacting a powder using a punch and die.

The term "disintegrating" or "disintegrate" refers to the act of undoing the physical solid integrity of, to break into parts, and/or to fall apart. The term "dissolve" or "dissolving" refers to the act of disintegrating chemically into a solution by immersion into a liquid.

The term "osmotic dosage form" refers to a controlled release delivery system in the form of a tablet. The tablet has a rigid water-permeable jacket with one or more laser drilled small holes. As the tablet is introduced to aqueous fluid, the osmotic pressure of water entering the tablet pushes the inner components of the tablet through the opening in the tablet.

The term "separation member" or "barrier" refers to an article used to physically separate two or more substances.

The term "membrane" refers to a selective barrier. At times, it is also an outer covering of cell or cell organelle that allows the passage of certain constituents and retains other constituents found in the liquid. The influent of a membrane is known as the feed-stream, the liquid that passes through the membrane is known as the permeate and the liquid containing the retained constituents is the retentate or concentrate. The degree of selectivity of a membrane depends on the membrane pore size. Depending on the pore size, they can be classified as microfiltration (MF), ultrafiltration (UF), nanofiltration (NF) and reverse osmosis (RO) membranes. Membranes can also be of various thickness, with homogeneous or heterogeneous structure. Membranes can be neutral or charged, and particle transport can be active or passive. The latter can be facilitated by pressure, concentration, chemical or electrical gradients of the membrane process. Membranes can be generally classified into synthetic membranes and biological membranes.

The term "Coagulase-negative staphylococci" refers to a species of *Staphylococcus*. The *Staphylococcus* genus includes at least 40 species. Common abbreviations for coagulase-negative *staphylococcus* species are CoNS and CNS.

The term "*Haemophilus*" refers to a genus of Gram-negative, pleomorphic, coccobacilli bacteria belonging to the Pasteurellaceae family. While *Haemophilus* bacteria are typically small coccobacilli they are categorized as pleomorphic bacteria because of the wide range of shapes they occasionally assume. The genus includes commensal organisms along with some significant pathogenic species such as *H. influenzae*—a cause of sepsis and bacterial meningitis in young children—and *H. ducreyi*, the causative agent of chancroid. All members are either aerobic or facultatively anaerobic.

The term "*Corynebacteriumn*" refers to a genus of Gram-positive, rod-shaped bacteria. They are widely distributed in nature and are mostly innocuous. Some are useful in industrial settings such as *C. glutamicum*. Others can cause human disease. *C. diphtheriae*, for example, is the pathogen responsible for diphtheria.

The term "*Propionibacterium*" refers to a Gram-positive, rod-shaped genus of bacteria named for their unique metabolism: They are able to synthesize propionic acid by using unusual transcarboxylase enzymes. Its members are primarily facultative parasites and commensals of humans and other animals, living in and around the sweat glands, sebaceous glands, and other areas of the skin. They are virtually ubiquitous and do not cause problems for most people, but propionobacteria have been implicated in acne and other skin conditions. Members of the genus *Propionibacterium* are widely used in the production of vitamin B12, tetrapyrrole compounds, and propionic acid, as well as in the probiotics and cheese industries.

The term "*Viridans streptococci*" refers to a large group of commensal streptococcal bacteria species that are either α-hemolytic, producing a green coloration on blood agar plates (hence the name "*viridans*"), or nonhemolytic. The pseudotaxonomic non-Linnean term *Streptococcus viridans* is often used to refer to this group of species, but writers that do not like to use the pseudotaxonomic term (which treats a group of species as if they were one species) prefer the terms *viridans* streptococci or *viridans* streptococcal species.

The term "saline solution" refers to a liquid solution that includes, at a minimum, water and salt (sodium chloride). For use with contact lenses, saline solutions are available in various formulations.

The term "neutralize" refers to the act of acidifying (lowering the pH of) a basic solution (a solution with a pH>7) or basifying (raising the pH of) an acidic solution (a solution with a pH<7), such that the resulting pH is approximately neutral (about 7).

Specific ranges, values, and embodiments provided below are for illustration purposes only and do not otherwise limit the scope of the disclosed subject matter, as defined by the claims.

Specific Ranges, Values, and Embodiments

In specific embodiments, the sterilized solution includes peracetic acid (PAA).

In specific embodiments, the sterilized solution includes peracetic acid (PAA), present in at least about 70 ppm of the sterilized solution. In further embodiments, the PAA is present in at least about 500 ppm of the sterilized solution.

In specific embodiments, the sterilized solution includes at least one of hydrogen peroxide, peracetic acid (PAA), acetic acid, water, acetic acid, and 1-hydroxyethylidene-1,1-diphosphonic acid.

In specific embodiments, the sterilized solution includes hydrogen peroxide, peracetic acid (PAA), acetic acid, water, acetic acid, and 1-hydroxyethylidene-1,1-diphosphonic acid.

In specific embodiments, the sterilized solution includes:

| Compound | % by weight | % range |
|---|---|---|
| Hydrogen peroxide (35%) | 1.03 | 0.8-1.2 |
| Acetic acid (100%) | 5.00 | 4.9-5.5 |
| Peracetic Acid | 0.08 | 0.06-0.1 |
| 1-Hydroxyethylidene-1,1-diphosphonic acid | 0.50 | 0.1-1.0 |
| Water | 93.39 | 92-95 |

In specific embodiments, the sterilized solution has a pH of less than about 8.0.

In specific embodiments, the buffering agent includes at least one of a bicarbonate, bisulfate, phosphate, thiosulfate, and alkali hydroxide.

In specific embodiments, the buffering agent is part of a buffering solution, which includes at least one of:

1) dextrose, lecithin, Polyoxyethylene (20) sorbitan monooleate (Tween 80), sodium bisulfate, sodium thioglycolate, sodium thiosulfate, tryptone, yeast extract, and deionized (DI) water;

2) columbia broth, sodium thiosulfate, potassium dihydrogen phosphate ($KH_2PO_4$), sodium hydroxide (NaOH), and deionized (DI) water;

3) Polyoxyethylene (20) sorbitan monooleate (Tween 80), sodium bisulfate, sodium thiosulfate, sodium thioglycolate, L-cystine, tryptone, sodium chloride, and deionized (DI) water;

4) letheen broth, sodium thiosulfate, catalase, and deionized (DI) water; and 5) letheen broth, sodium thiosulfate, iron, sodium bicarbonate, and deionized (DI) water.

In specific embodiments, the buffering agent is part of a buffering solution, which includes at least one of:

1) 5.0 g dextrose, 3.5 g lecithin, 2.5 g Polyoxyethylene (20) sorbitan monooleate (Tween 80), 1.25 g sodium bisulfate, 0.5 g sodium thioglycolate, 3.9 g sodium thiosulfate, 2.5 g tryptone, and 1.25 g yeast extract, per 500 ml of deionized (DI) water;

2) 17.5 g columbia broth, 2.5 g sodium thiosulfate, 13.0 g potassium dihydrogen phosphate ($KH_2PO_4$), and 2.5 g sodium hydroxide (NaOH), per 500 ml of deionized (DI) water;

3) 32.25 g Polyoxyethylene (20) sorbitan monooleate (Tween 80), 2.5 g sodium bisulfate, 3.9 g sodium thiosulfate, 2.5 g sodium thioglycolate, 0.75 g L-cystine, 1.0 g tryptone, and 8.5 g sodium chloride, per 500 ml of deionized (DI) water;

4) 12.85 g letheen broth, 5.0 g sodium thiosulfate, and 0.01 wt. % catalase, per 500 ml of deionized (DI) water; and 5) 15 g letheen broth, 5 g sodium thiosulfate, 3 g iron, 5 g sodium bicarbonate, and 500 ml deionized (DI) water.

In specific embodiments, the buffering agent is part of a buffering solution, which includes at least one of a silver-containing compound, an iron-containing compound, or a combination thereof, having at least one of the following oxidation states: $Ag^{3+}$, $Ag^{2+}$, $Ag^{1+}$, $Fe^{6+}$, $Fe^{5+}$, $Fe^{4+}$, $Fe^{3+}$, $Fe^{2+}$, $Fe^{1+}$, $Fe^{-1}$, and $Fe^{2-}$.

In specific embodiments, the buffering agent is part of a buffering solution, which includes silver nitrate ($AgNO_3$).

In specific embodiments, the buffering agent is part of a buffering solution, which includes an iron-containing compound having the oxidation state $Fe^{2+}$ (ferrous).

In specific embodiments, the buffering agent is part of a buffering solution, which includes an iron-containing compound having the oxidation state $Fe^{3+}$ (ferric).

In specific embodiments, the buffering agent is present in an amount sufficient to raise the pH of the sterilized solution to at least about 6.

In specific embodiments, the buffering agent is configured as a unit solid mass.

In specific embodiments, the buffering agent is configured as a solid pellet, a solid pill, a solid capsule, a solid tablet, a solid disintegrating tablet, or a solid osmotic dosage form.

In specific embodiments, the buffering agent is configured as a unit solid mass, which is adhered to an inside surface of the container.

In specific embodiments, the container includes a separation member.

In specific embodiments, the container includes a separation member, such that the separation member effectively provides for a physical separation between the (i) sterilized solution and contact lens and (ii) buffering agent.

In specific embodiments, the container includes a separation member, wherein the separation member includes at least one of a membrane, push-tab, pull-tab and sta-tab.

In specific embodiments, the system is safe and effective for the shipping, storage, and handling of a sterilized contact lens.

In specific embodiments, the system further includes printed indicia located on the container.

In specific embodiments, the sterilized solution is essentially free of microorganisms and pathogens.

In specific embodiments, the sterilized solution is essentially free of microorganisms and pathogens selected from the group consisting of: (1) Coagulase-negative staphylococci, (2) *Haemophilus*, (3) *Corynebacterium*, (4) *Propionibacterium*, (5) *Viridans* streptococci, and combinations thereof.

In specific embodiments, the system includes two contacts lens.

In specific embodiments, the system further includes packaging material that contains the system.

In specific embodiments, the system further includes packaging material that contains the system, the packaging material also containing printed indicia located therein, the printed indicia instructing the user to rinse the contact lens and place in the eye.

In specific embodiments, the sterilized solution is a liquid disinfectant.

In specific embodiments, the system further includes printed indicia located on the container, the printed indicia instructing the user to rinse the contact lens and place in the eye.

Methods for Neutralizing a Sterilized Contact Lens Solution:

In specific embodiments, the contact lens and sterilized solution are in physical contact in step (i), for at least about 2 hours.

In specific embodiments, the contact lens and sterilized solution are in physical contact in step (i), for a period of time sufficient to obtain at least about a 6.26 log reduction against bacterial endospores.

In specific embodiments, the contact lens and sterilized solution are in physical contact in step (i), for a period of time sufficient to obtain a sterility assurance level (SAL) of about 10-6.

In specific embodiments, the method for neutralizing a sterilized contact lens solution further including (iii) rinsing the contact lens and (iv) inserting the contact lens onto the outer surface of an eye.

In specific embodiments, two contact lenses are inserted, each independently onto a surface of an eye.

In specific embodiments, prior to inserting the contact lens, the user's hands are washed and dried.

Method of Inserting a Contact Lens onto the Outer Surface of an Eye:

In specific embodiments, two contact lenses are inserted, each independently onto a surface of an eye.

Enumerated Examples of the Invention

The following enumerated Example 1 to Example 43 are provided for further illustration and description. All combinations and sub-combinations embraced within the enumerated examples below are contemplated herein and form part of the present invention, as defined by the claims.

Example 1

The present invention provides a system comprising:
(a) sterilized solution;
(b) at least one contact lens located substantially in the sterilized solution;
(c) buffering agent; and
(d) container that contains the sterilized solution, contact lens, and buffering agent;

wherein the sterilized solution and contact lens are physically separated from the buffering agent.

Example 2

The system of the above Example, wherein the sterilized solution comprises peracetic acid (PAA).

Example 3

The system of any one of the above Examples, wherein the sterilized solution comprises peracetic acid (PAA), present in at least about 70 ppm of the sterilized solution or in at least about 500 ppm of the sterilized solution.

Example 4

The system of any one of the above Examples, wherein the sterilized solution comprises at least one of hydrogen peroxide, peracetic acid (PAA), acetic acid, water, acetic acid, and 1-hydroxyethylidene-1,1-diphosphonic acid.

Example 5

The system of any one of the above Examples, wherein the sterilized solution comprises hydrogen peroxide, peracetic acid (PAA), acetic acid, water, acetic acid, and 1-hydroxyethylidene-1,1-diphosphonic acid.

Example 6

The system of any of the above Examples, wherein the sterilized solution comprises:

| Compound | % by weight | % range |
| --- | --- | --- |
| Hydrogen peroxide (35%) | 1.03 | 0.8-1.2 |
| Acetic acid (100%) | 5.00 | 4.9-5.5 |
| Peracetic Acid | 0.08 | 0.06-0.1 |
| 1-Hydroxyethylidene-1,1-diphosphonic acid | 0.50 | 0.1-1.0 |
| Water | 93.39 | 92-95 |

Example 7

The system of any one of the above Examples, wherein the sterilized solution has a pH of less than about 8.0.

Example 8

The system of any one of the above Examples, wherein the buffering agent comprises at least one of a bicarbonate, bisulfate, phosphate, thiosulfate, and alkali hydroxide.

Example 9

The system of any one of the above Examples, wherein the buffering agent is part of a buffering solution, which comprises at least one of:
1) dextrose, lecithin, Polyoxyethylene (20) sorbitan monooleate (Tween 80), sodium bisulfate, sodium thioglycolate, sodium thiosulfate, tryptone, yeast extract, and deionized (DI) water;
2) columbia broth, sodium thiosulfate, potassium dihydrogen phosphate ($KH_2PO_4$), sodium hydroxide (NaOH), and deionized (DI) water;
3) Polyoxyethylene (20) sorbitan monooleate (Tween 80), sodium bisulfate, sodium thiosulfate, sodium thioglycolate, L-cystine, tryptone, sodium chloride, and deionized (DI) water;
4) letheen broth, sodium thiosulfate, catalase, and deionized (DI) water; and
5) letheen broth, sodium thiosulfate, iron, sodium bicarbonate, and deionized (DI) water.

Example 10

The system of any one of the above Examples, wherein the buffering agent is part of a buffering solution, which comprises at least one of:
1) 5.0 g dextrose, 3.5 g lecithin, 2.5 g Polyoxyethylene (20) sorbitan monooleate (Tween 80), 1.25 g sodium bisulfate, 0.5 g sodium thioglycolate, 3.9 g sodium thiosulfate, 2.5 g tryptone, and 1.25 g yeast extract, per 500 ml of deionized (DI) water;
2) 17.5 g columbia broth, 2.5 g sodium thiosulfate, 13.0 g potassium dihydrogen phosphate ($KH_2PO_4$), and 2.5 g sodium hydroxide (NaOH), per 500 ml of deionized (DI) water;
3) 32.25 g Polyoxyethylene (20) sorbitan monooleate (Tween 80), 2.5 g sodium bisulfate, 3.9 g sodium thiosulfate, 2.5 g sodium thioglycolate, 0.75 g L-cystine, 1.0 g tryptone, and 8.5 g sodium chloride, per 500 ml of deionized (DI) water;

4) 12.85 g letheen broth, 5.0 g sodium thiosulfate, and 0.01 wt. % catalase, per 500 ml of deionized (DI) water; and 5) 15 g letheen broth, 5 g sodium thiosulfate, 3 g iron, 5 g sodium bicarbonate, and 500 ml deionized (DI) water.

Example 11

The system of any one of the above Examples, wherein the buffering agent is part of a buffering solution, which comprises at least one of a silver-containing compound, an iron-containing compound, or a combination thereof, having at least one of the following oxidation states: $Ag^{3+}$, $Ag^{2+}$, $Ag^{1+}$, $Fe^{6+}$, $Fe^{5+}$, $Fe^{4+}$, $Fe^{3+}$, $Fe^{2+}$, $Fe^{1+}$, $Fe^{-1}$, and $Fe^{2-}$.

Example 12

The system of any one of the above Examples, wherein the buffering agent is part of a buffering solution, which comprises silver nitrate ($AgNO_3$).

Example 13

The system of any one of the above Examples, wherein the buffering agent is part of a buffering solution, which comprises an iron-containing compound having the oxidation state $Fe^{2+}$ (ferrous).

Example 14

The system of any one of the above Examples, wherein the buffering agent is part of a buffering solution, which comprises an iron-containing compound having the oxidation state $Fe^{3+}$ (ferric).

Example 15

The system of any one of the above Examples, wherein the buffering agent is present in an amount sufficient to raise the pH of the sterilized solution to at least about 6.

Example 16

The system of any one of the above Examples, wherein the buffering agent is configured as a unit solid mass.

Example 17

The system of any one of the above Examples, wherein the buffering agent is configured as a solid pellet, a solid pill, a solid capsule, a solid tablet, a solid disintegrating tablet, or a solid osmotic dosage form.

Example 18

The system of any one of the above Examples, wherein the buffering agent is configured as a unit solid mass, which is adhered to an inside surface of the container.

Example 19

The system of any one of the above Examples, wherein the container comprises a separation member.

Example 20

The system of any one of the above Examples, wherein the container comprises a separation member, such that the separation member effectively provides for a physical separation between the (i) sterilized solution and contact lens and (ii) buffering agent.

Example 21

The system of any one of the above Examples, wherein the container comprises a separation member, wherein the separation member comprises at least one of a membrane, push-tab, pull-tab and sta-tab.

Example 22

The system of any one of the above Examples, which is safe and effective for the shipping, storage, and handling of a sterilized contact lens.

Example 23

The system of any one of the above Examples, further comprising printed indicia located on the container.

Example 24

The system of any one of the above Examples, wherein the sterilized solution is essentially free of microorganisms and pathogens.

Example 25

The system of any one of the above Examples, wherein the sterilized solution is essentially free of microorganisms and pathogens selected from the group consisting of: (1) Coagulase-negative staphylococci, (2) *Haemophilus*, (3) *Corynebacterium*, (4) *Propionibacterium*, (5) *Viridans* streptococci, and combinations thereof.

Example 26

The system of any one of the above Examples, comprising two contacts lens.

Example 27

The system of any one of the above Examples, further comprising packaging material that contains the system.

Example 28

The system of any one of the above Examples, further comprising packaging material that contains the system, the packaging material also containing printed indicia located therein, the printed indicia instructing the user to rinse the contact lens and place in the eye.

Example 29

The system of any one of the above Examples, wherein the sterilized solution is a liquid disinfectant.

Example 30

The system of any one of the above Examples, further comprising printed indicia located on the container, the printed indicia instructing the user to rinse the contact lens and place in the eye.

Example 31

The present invention provides a method for neutralizing a sterilized contact lens solution, the method comprising:

(i) providing or forming any one of the systems of Examples 1 to 30 or a system comprising:
   (a) sterilized solution;
   (b) at least one contact lens located substantially in the sterilized solution;
   (c) buffering agent; and
   (d) container that contains the sterilized solution, contact lens, and buffering agent;
to obtain a sterilized contact lens solution, wherein the sterilized solution and contact lens are physically separated from the buffering agent; and
   (ii) facilitating physical contact between the (0.1) sterilized solution and contact lens and (2) buffering agent, wherein the contact is effective to neutralize the sterilized contact lens solution.

Example 32

The method of Example 31, wherein the contact lens and sterilized solution are in physical contact in step (i), for at least about 2 hours.

Example 33

The method of any one of Examples 31 or 32, wherein the contact lens and sterilized solution are in physical contact in step (i), for a period of time sufficient to obtain at least about a 6.26 log reduction against bacterial endospores.

Example 34

The method of any one of the above Examples, wherein the contact lens and sterilized solution are in physical contact in step (i), for a period of time sufficient to obtain a sterility assurance level (SAL) of about 10-6.

Example 35

The method of any one of the above Examples, further comprising
   (iii) rinsing the contact lens and (iv) inserting the contact lens onto the outer surface of an eye.

Example 36

The method of any one of the above Examples, wherein two contact lenses are inserted, each independently onto a surface of an eye.

Example 37

The method of any one of the above Examples, wherein prior to inserting the contact lens, the user's hands are washed and dried.

Example 38

The present invention provides a method of inserting a contact lens onto the outer surface of an eye, the method comprising:
   (i) providing or forming any one of the systems of Examples 1 to 30 or a system comprising:
      (a) sterilized solution;
      (b) at least one contact lens located substantially in the sterilized solution;
      (c) buffering agent; and
      (d) container that contains the sterilized solution, contact lens, and buffering agent;
to obtain a sterilized contact lens solution, wherein the sterilized solution and contact lens are physically separated from the buffering agent;
   (ii) facilitating physical contact between the (1) sterilized solution and contact lens and (2) buffering agent, effective to neutralize the sterilized contact lens solution;
   (iii) optionally rinsing the contact lens; and
   (iv) inserting the contact lens onto the outer surface of an eye.

Example 39

The method of Example 38, wherein two contact lenses are inserted, each independently onto a surface of an eye.

Example 40

The method of any one of Examples 38 or 39, wherein prior to inserting the contact lens, the user's hands are washed and dried.

Example 41

The method of any one of Examples 38 to 40, wherein prior to inserting the contact lens, the contact lens is rinsed with a sterile saline solution.

Example 42

The present invention provides a method of disinfecting and neutralizing a contact lens, the method comprising:
   (i) providing or forming any one of the systems of Examples 1 to 30 or a system comprising:
      (a) sterilized solution;
      (b) at least one contact lens located substantially in the sterilized solution;
      (c) buffering agent; and
      (d) container that contains the sterilized solution, contact lens, and buffering agent;
to obtain a sterilized contact lens solution, wherein the sterilized solution and contact lens are physically separated from the buffering agent; and
   (ii) facilitating physical contact between the (1) sterilized solution and contact lens and (2) buffering agent, effective to neutralize the sterilized contact lens solution.

Example 43

The method of Example 42, further comprising:
   (iii) optionally rinsing the contact lens; and
   (iv) inserting the contact lens onto the outer surface of an eye.

Each of these non-limiting examples can stand on its own, or can be combined in various permutations or combinations with one or more of the other examples.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B." unless otherwise indicated. In this document, the terms "including"

and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel". "perpendicular". "round", or "square", are not intended to require absolute mathematical precision, unless the context indicates otherwise. Instead, such geometric terms allow for variations due to manufacturing or equivalent functions. For example, if an element is described as "round" or "generally round." a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A system comprising:
   (a) sterilized solution;
   (b) at least one contact lens located substantially in the sterilized solution;
   (c) buffering agent; and
   (d) container that contains the sterilized solution, contact lens, and buffering agent; wherein the sterilized solution and contact lens are physically separated from the buffering agent, and wherein the buffering agent is part of a buffering solution which comprises at least one of
   (1) dextrose, lecithin, polysorbate 80, sodium bisulfate, sodium thioglycolate, sodium thiosulfate, tryptone, yeast extract, and deionized (DI) water;
   (2) columbia broth, sodium thiosulfate, potassium dihydrogen phosphate ($KH_2PO_4$), sodium hydroxide (NaOH), and deionized (DI) water;
   (3) polysorbate 80, sodium bisulfate, sodium thiosulfate, sodium thioglycolate, L-cystine, tryptone, sodium chloride, and deionized (DI) water;
   (4) letheen broth, sodium thiosulfate, catalase, and deionized (DI) water; and
   (5) letheen broth, sodium thiosulfate, iron, sodium bicarbonate, and deionized (DI) water.

2. The system of claim 1, wherein the sterilized solution comprises peracetic acid (PAA), present in at least about 500 ppm of the sterilized solution.

3. The system of claim 1, wherein the sterilized solution comprises hydrogen peroxide, peracetic acid (PAA), acetic acid, water, acetic acid, and 1-hydroxyethylidene-1,1-diphosphonic acid.

4. The system of claim 1, wherein the sterilized solution comprises hydrogen peroxide (35%) in an amount that is between 0.8 and 1.2 wt. % of the sterilized solution, acetic acid (100%) in an amount that is between 4.9 and 5.5 wt. % of the sterilized solution, peracetic acid in an amount that is between 0.06 and 0.1 wt. % of the sterilized solution, 1-Hydroxyethylidene-1,1-diphosphonic acid in an amount that is between 0.1 and 1.0 wt. % of the sterilized solution, and water in an amount that is between 92 and 95 wt. % of the sterilized solution.

5. The system of claim 1, wherein the sterilized solution has a pH of less than about 8.0.

6. The system of claim 1, wherein the buffering agent is part of a buffering solution, which comprises at least one of:
   1) 5.0 g dextrose, 3.5 g lecithin, 2.5 g polysorbate 80, 1.25 g sodium bisulfate, 0.5 g sodium thioglycolate, 3.9 g sodium thiosulfate, 2.5 g tryptone, and 1.25 g yeast extract, per 500 ml of deionized (DI) water;
   2) 17.5 g columbia broth, 2.5 g sodium thiosulfate, 13.0 g potassium dihydrogen phosphate ($KH_2PO_4$), and 2.5 g sodium hydroxide (NaOH), per 500 ml of deionized (DI) water;
   3) 32.25 g polysorbate 80, 2.5 g sodium bisulfate, 3.9 g sodium thiosulfate, 2.5 g sodium thioglycolate, 0.75 g L-cystine, 1.0 g tryptone, and 8.5 g sodium chloride, per 500 ml of deionized (DI) water;
   4) 12.85 g letheen broth, 5.0 g sodium thiosulfate, and 0.01 wt. % catalase, per 500 ml of deionized (DI) water; and
   5) 15 g letheen broth, 5 g sodium thiosulfate, 3 g iron, 5 g sodium bicarbonate, and 500 ml deionized (DI) water.

7. The system of claim 1, wherein the buffering agent is part of a buffering solution, which comprises at least one of a silver-containing compound, an iron-containing compound, or a combination thereof, having at least one of the following oxidation states:

$Ag3+, Ag2+, Ag1+, Fe6+, Fe5+, Fe4+, Fe3+, Fe2+, Fe1+, Fe-1$, and $Fe2-$.

8. The system of claim 1, wherein the buffering agent is part of a buffering solution, which comprises silver nitrate ($AgNO3$).

9. The system of claim 1, wherein the buffering agent is present in an amount sufficient to raise the pH of the sterilized solution to at least about 6.

10. The system of claim 1, wherein the buffering agent is configured as a unit solid mass.

11. The system of claim 1, wherein the buffering agent is configured as a solid pellet, a solid pill, a solid capsule, a solid tablet, a solid disintegrating tablet, or a solid osmotic dosage form.

12. The system of claim 1, wherein the buffering agent is configured as a unit solid mass, which is adhered to an inside surface of the container.

13. The system of claim 1, wherein the container comprises a separation member.

14. The system of claim 1, wherein the container comprises a separation member, such that the separation member effectively provides for a physical separation between the (i) sterilized solution and contact lens and (ii) buffering agent.

15. The system of claim 1, wherein the container comprises a separation member, wherein the separation member comprises at least one of a membrane, push-tab, pull-tab and sta-tab.

16. A method for neutralizing a sterilized contact lens solution, the method comprising:
  (i) providing or forming a system comprising:
    (a) sterilized solution;
    (b) at least one contact lens located substantially in the sterilized solution;
    (c) buffering agent; and
    (d) container that contains the sterilized solution, contact lens, and buffering agent;
  to obtain a sterilized contact lens solution, wherein the sterilized solution and contact lens are physically separated from the buffering agent, and wherein the buffering agent is part of a buffering solution which comprises at least one of
    (1) dextrose, lecithin, polysorbate 80, sodium bisulfate, sodium thioglycolate, sodium thiosulfate, tryptone, yeast extract, and deionized (DI) water;
    (2) columbia broth, sodium thiosulfate, potassium dihydrogen phosphate ($KH_2PO_4$), sodium hydroxide (NaOH), and deionized (DI) water;
    (3) polysorbate 80, sodium bisulfate, sodium thiosulfate, sodium thioglycolate, L-cystine, tryptone, sodium chloride, and deionized (DI) water;
    (4) letheen broth, sodium thiosulfate, catalase, and deionized (DI) water; and
    (5) letheen broth, sodium thiosulfate, iron, sodium bicarbonate, and deionized (DI) water; and
  (ii) facilitating physical contact between the (1) sterilized solution and contact lens and (2) buffering agent, wherein the contact is effective to neutralize the sterilized contact lens solution.

17. The method of claim 16, wherein the contact lens and sterilized solution are in physical contact in step (i), for a period of time sufficient to obtain at least about a 6.26 log reduction against bacterial endospores.

18. The method of claim 16, wherein the contact lens and sterilized solution are in physical contact in step (i), for a period of time sufficient to obtain a sterility assurance level (SAL) of about 10-6.

19. A method of inserting a contact lens onto the outer surface of an eye, the method comprising:
  (i) providing or forming a system comprising:
    (a) sterilized solution;
    (b) at least one contact lens located substantially in the sterilized solution;
    (c) buffering agent; and
    (d) container that contains the sterilized solution, contact lens, and buffering agent;
  to obtain a sterilized contact lens solution, wherein the sterilized solution and contact lens are physically separated from the buffering agent, and wherein the buffering agent is part of a buffering solution which comprises at least one of
    (1) dextrose, lecithin, polysorbate 80, sodium bisulfate, sodium thioglycolate, sodium thiosulfate, tryptone, yeast extract, and deionized (DI) water;
    (2) columbia broth, sodium thiosulfate, potassium dihydrogen phosphate ($KH_2PO_4$), sodium hydroxide (NaOH), and deionized (DI) water;
    (3) polysorbate 80, sodium bisulfate, sodium thiosulfate, sodium thioglycolate, L-cystine, tryptone, sodium chloride, and deionized (DI) water;
    (4) letheen broth, sodium thiosulfate, catalase, and deionized (DI) water; and
    (5) letheen broth, sodium thiosulfate, iron, sodium bicarbonate, and deionized (DI) water;
  (ii) facilitating physical contact between the (1) sterilized solution and contact lens and (2) buffering agent, effective to neutralize the sterilized contact lens solution;
  (iii) optionally rinsing the contact lens; and
  (iv) inserting the contact lens onto the outer surface of an eye.

20. The system of claim 1, wherein the sterilized solution comprises hydrogen peroxide (35%) in an amount that is 1.03 wt. % of the sterilized solution, acetic acid (100%) in an amount that is 5.00 wt. % of the sterilized solution, peracetic acid in an amount that is 0.08 wt. % of the sterilized solution, 1-Hydroxyethylidene-1,1-diphosphonic acid in an amount that is 0.50 wt. % of the sterilized solution, and water in an amount that is 93.39 wt. % of the sterilized solution.

21. The system of claim 1, wherein the sterilized solution consists of hydrogen peroxide, peracetic acid (PAA), acetic acid, water, acetic acid, and 1-hydroxyethylidene-1,1-diphosphonic acid.

22. The system of claim 1, wherein the sterilized solution consists of hydrogen peroxide (35%) in an amount that is between 0.8 and 1.2 wt. % of the sterilized solution, acetic acid (100%) in an amount that is between 4.9 and 5.5 wt. % of the sterilized solution, peracetic acid in an amount that is between 0.06 and 0.1 wt. % of the sterilized solution, 1-Hydroxyethylidene-1,1-diphosphonic acid in an amount that is between 0.1 and 1.0 wt. % of the sterilized solution, and water in an amount that is between 92 and 95 wt. % of the sterilized solution.

\* \* \* \* \*